(12) United States Patent
Lesmeister

(10) Patent No.: US 10,327,931 B2
(45) Date of Patent: Jun. 25, 2019

(54) PUSHER-ASSEMBLY FOR AN INSERTION SYSTEM FOR A SELF-EXPANDABLE VASCULAR IMPLANT

(71) Applicant: JOTEC GmbH, Hechingen (DE)

(72) Inventor: Rainer Lesmeister, Wannweil (DE)

(73) Assignee: JOTEC GmbH, Hechingen (DE)

( * ) Notice: Subject to any disclaimer, the term of this patent is extended or adjusted under 35 U.S.C. 154(b) by 428 days.

(21) Appl. No.: 14/930,562

(22) Filed: Nov. 2, 2015

(65) Prior Publication Data

US 2016/0051387 A1 Feb. 25, 2016

Related U.S. Application Data

(63) Continuation of application No. PCT/EP2014/058258, filed on Apr. 23, 2014.

(30) Foreign Application Priority Data

May 3, 2013 (DE) .......................... 10 2013 104 565

(51) Int. Cl.
*A61F 2/966* (2013.01)
(52) U.S. Cl.
CPC .................................... *A61F 2/966* (2013.01)
(58) Field of Classification Search
CPC .... A61F 2/966; A61F 2/95; A61F 2002/9505; A61F 2002/9522; A61F 2002/9534
See application file for complete search history.

(56) References Cited

U.S. PATENT DOCUMENTS

| 6,607,551 B1 * | 8/2003 | Sullivan ................... A61F 2/95 623/1.11 |
| 8,206,413 B2 | 6/2012 | Jones et al. |
| 2002/0045929 A1 | 4/2002 | Diaz |

(Continued)

FOREIGN PATENT DOCUMENTS

| WO | WO 1998/04189 A1 | 2/1998 |
| WO | WO 2007/005799 A1 | 1/2007 |

(Continued)

OTHER PUBLICATIONS

International Search Report from parent PCT/EP2014/058258, 3 pages (dated Aug. 6, 2014).

*Primary Examiner* — Thomas M McEvoy
(74) *Attorney, Agent, or Firm* — Klarquist Sparkman, LLP

(57) ABSTRACT

The invention relates to a pusher assembly for an insertion system for a vascular implant. The pusher assembly has a catheter tube. The catheter tube has a tubular cavity for accommodating a guide wire and has a proximal catheter tube segment and a distal catheter tube segment adjoining the proximal catheter tube segment. The distal catheter tube segment is provided at least partially for movably accommodating a vascular implant on the distal catheter tube segment. The catheter tube also has a pusher unit for releasing the vascular implant, said pusher unit being proximally adjacent to a vascular implant loaded onto catheter tube. The pusher assembly is characterized in that the pusher unit is formed by individual, segment-like elements, which are arranged on behind the other and adjacent to each other and are arranged on the catheter tube in order to proximally adjoin the vascular implant.

9 Claims, 3 Drawing Sheets

(56) References Cited

U.S. PATENT DOCUMENTS

2007/0118207 A1* 5/2007 Amplatz .................. A61F 2/95
                                                    623/1.12
2013/0289698 A1* 10/2013 Wang .................... A61F 2/2436
                                                    623/1.12

FOREIGN PATENT DOCUMENTS

WO   WO 2008/088391 A2   7/2008
WO   WO 2011/008538      1/2011

* cited by examiner

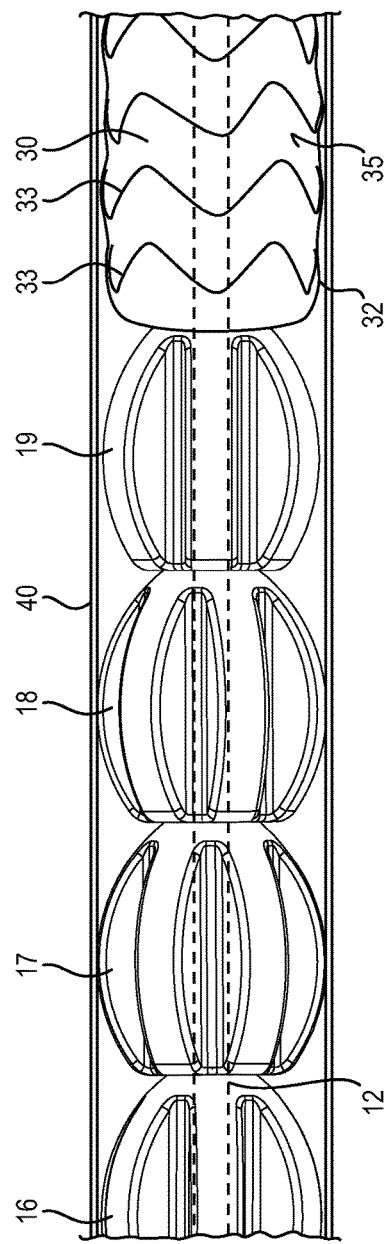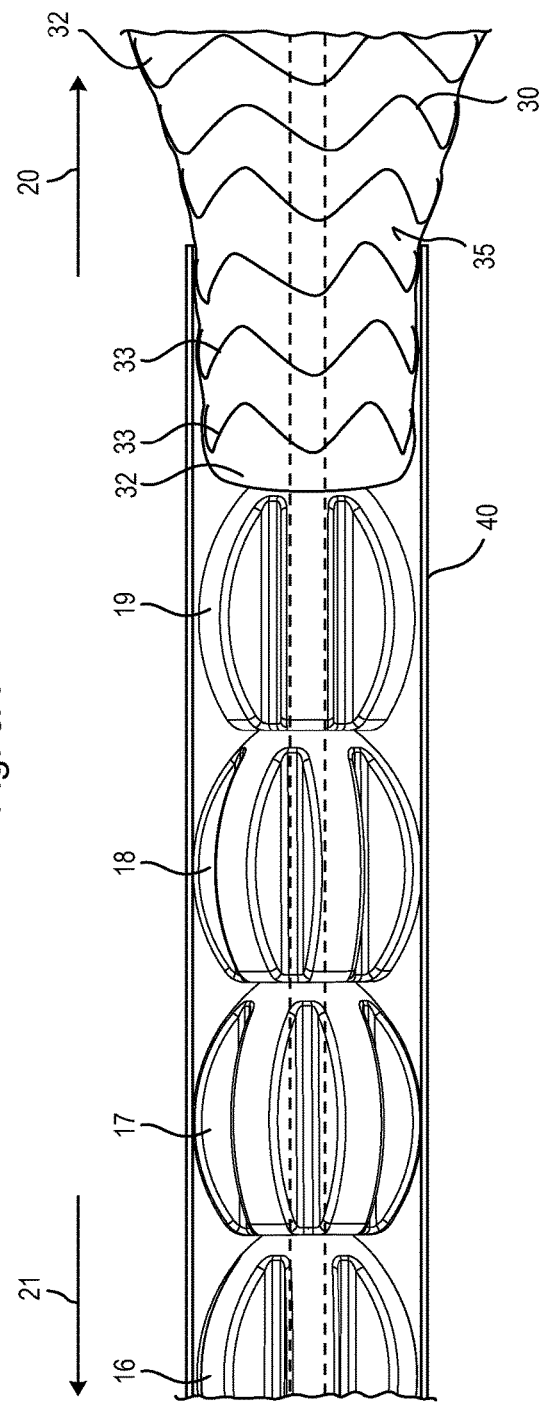

PUSHER-ASSEMBLY FOR AN INSERTION SYSTEM FOR A SELF-EXPANDABLE VASCULAR IMPLANT

CROSS REFERENCE TO RELATED APPLICATIONS

This is a continuation of international patent application PCT/EP2014/058258, filed on Apr. 23, 2014, designating the U.S., which claims priority from German patent application DE 10 2013 104 565.0, filed on May 3, 2013. The entire contents of these priority applications are incorporated herein by reference.

BACKGROUND OF THE INVENTION

The present invention relates to a pusher assembly for an insertion system for a self-expanding vascular implant, wherein the pusher assembly has a catheter tube which has a lumen for accommodating a guide wire and which has a first, proximal catheter tube portion and, adjoining the latter, a second, distal catheter tube portion, wherein the distal catheter tube portion is provided at least partially for movably accommodating a vascular implant thereon, and wherein the catheter tube moreover has a pusher unit for releasing the vascular implant, said pusher unit being proximally adjacent to a vascular implant loaded onto the catheter tube.

Insertion systems for inserting and releasing vascular implants in vessels of a patient, which insertion systems have the aforementioned pusher assembly, are known in the prior art. With insertion systems of this kind, vascular implants, which are also referred to as endovascular stents or stent grafts, for example for treatment of aneurysms or for keeping vessels open, are generally implanted into the vessels to be treated.

The vascular implants presently in use are mainly composed of a hollow cylindrical metal frame, of which the jacket surface is covered by a textile or polymer material, such that a hollow cylindrical body is obtained, which is also referred to as a stent graft or covered stent, whereas braided or laser-cut or twisted metal wire meshes that are not covered about the circumference by a textile or polymer material are referred to as stents or uncovered stents.

For implantation, the vascular implant is radially compressed such that its cross-sectional area is considerably reduced. For introduction into a vessel of a patient, the vascular implant is introduced into the vessel with the aid of an insertion system and released. On account of the spring action of the metal frame, the vascular implant expands back to its original shape after its release and thus spreads open its jacket surface, which clamps itself inside the blood vessel and thereby either bridges the aneurysm or holds the blood vessel open by the spring action. To obtain the desired effect of a vascular implant, it is not only necessary for it to be positioned such that, particularly in the case of an aneurysm, it is able to clamp itself sufficiently firmly in the corresponding blood vessel; the radial orientation of the vascular implant is also often of very great importance. This is particularly the case when further vessels branch off at or near the location where the vascular implant is to be implanted, since the introduction of the vascular implant must not adversely affect the supply to these branches. It is therefore extremely critical, especially at these locations, that the stent is not displaced in its longitudinal direction in the implantation.

For implantation, as has already been mentioned above, the vascular implants are radially compressed and are then positioned in the vessel, in the area thereof to be treated, with the aid of a guide wire, a guide wire catheter, onto which the vascular implant is generally loaded, a pusher rod and a proximal handling portion, and optionally with the aid of further additional known features. The correct position of the vascular implant can be monitored via X-ray markers, for example, which are provided on the guide wire, on the guide wire catheter, on the jacket of the stent, or at other locations.

To ensure that the vascular implants remain in a compressed state during the positioning, they are arranged in a sleeve or a tube that compresses the vascular implant radially inward. After the vascular implant has been positioned in the vessel, this so-called withdrawal sleeve is pulled back and, in order to fix the stent, it is held axially by what is called a pusher, which is arranged in the proximal direction. The pusher lies in contact with the vascular implant and holds the latter in its axial position, while the withdrawal sleeve also surrounding the pusher is pulled away from the vascular implant, which thus expands and clamps itself in the vessel.

At the start of the implantation step, a guide wire is first inserted into the vessel and advanced to the vessel area to be treated. As soon as the vessel area to be treated is reached, the distal part of the insertion device, i.e. the part which lies farther from the operator than the proximal part of the insertion system actuated by the operator and which encloses the guide wire catheter, the vascular implant and the pusher, is guided over the guide wire into the vessel and to the area to be treated. The guide wire catheter is generally provided with a flexible dilator tip at its distal end, in order to widen the vessel paths such that the insertion device and the vascular implant can be more easily received therein.

To ensure that the distal end of the insertion device has a certain degree of flexibility, the guide wire catheter, on which the vascular implant is carried during the insertion into the vessel, is generally flexible, such that this part in particular can adapt to the conditions of the treated vessel, in particular to the curvatures of the latter, and to the guide wire via which the guide wire catheter is inserted.

On the other hand, on account of the high forces that are exerted when pulling the withdrawal sleeve back in order to release the stent, it is necessary that the pusher is generally much stiffer than the guide wire catheter, so as to ensure a sufficiently strong abutment force against the proximally directed force that is exerted during the withdrawal of the withdrawal sleeve that compresses the vascular implant. For these reasons, the pusher is therefore generally much stiffer than the other components of the insertion system.

The withdrawal sleeves normally used in the prior art are generally composed of polymer tubes which are in most cases made from polyethylene or tetrafluoroethylene. The wall thickness of these polymer tubes is dimensioned such that it withstands the expansion pressure of the collapsed vascular implant, remains stable over the course of time and is not subject to any thermal creep. This means, however, that the withdrawal sleeve has a relatively high geometric moment of inertia of its cross-sectional profile. Moreover, withdrawal sleeves are relatively stiff in the axial direction, so that the operator does not lose control of the degree of release of the vascular implant. For these reasons, the pusher should also be stiffer than the withdrawal sleeve in the axial direction, so as to be able to sufficiently counteract the forces described above.

Therefore, the insertion systems known in the prior art generally comprise, in addition to an internal guide wire catheter, also a stiff pusher catheter tube and an outer sleeve tube or sleeve catheter.

It has now been shown that, especially in the case of patients with extremely tortuous vessels, the insertion systems known in the prior art can be used only with difficulty if at all, since the stiffness of the component parts, in particular of the pusher catheter tube, does not allow the insertion system and the vascular implant to be advanced through the tortuous vessels. In addition to the danger of perforation of the vessel wall, there is also the disadvantage that, with the insertion systems known in the prior art, the stent cannot be positioned with sufficient precision in highly tortuous vessels, and also that the withdrawal sleeve buckles, and that this buckling means that greater force has to be applied to overcome the kinks in the withdrawal sleeve. There is also a danger of the guide wire catheter buckling in relation to the pusher catheter tube guided over it, specifically at the transition point to the pusher catheter, and this likewise necessitates the discontinuation of the insertion procedure.

SUMMARY OF THE INVENTION

Against this background, the object of the present invention is to create a pusher assembly, and an insertion system having the pusher assembly, which is of the type mentioned at the outset and which avoids the aforementioned disadvantages. In particular, the novel pusher assembly is intended to permit increased flexibility of the insertion system, so as to be able also to treat patients whose vessels are highly tortuous.

According to the present invention, this object, along with others, is achieved by the fact that the pusher unit is formed by individual and similar segment-like elements, which are arranged one behind another and adjacent to one another on the catheter tube and proximally adjacent to the vascular implant.

The object of the invention is further achieved by an insertion system having the aforementioned pusher assembly according to the invention.

BRIEF DESCRIPTION OF THE DRAWINGS

An illustrative embodiment of the invention is shown in the accompanying figures and is described in more detail below with reference to these figures, in which:

FIG. 3A-3B shows a schematic and partial representation of the pusher assembly with the vascular implant arranged at the distal end, with a withdrawal sleeve arranged over it, in the still loaded state (FIG. 3A) and in the partially released state (FIG. 3B).

Figure 1A:
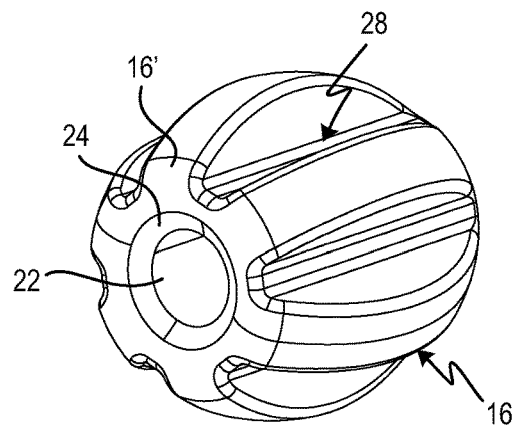
FIGS. 1A-1C shows a schematic representation of an individual segment-like element of the pusher assembly, in a perspective lateral view of the proximal opening (FIG. 1A), in a perspective lateral view of the distal opening (FIG. 1B), and in a direct lateral plan view (FIG. 1C)

The object of the invention is in this way achieved in full.

DETAILED DESCRIPTION

In the pusher assembly according to the invention, segment-like elements which are threaded onto the catheter tube, as it were like pearls, are present according to the invention, and their arrangement in series on the catheter tube results in the formation of a pusher unit which, on account of the stiffness of the individual segment-like elements, does not adversely affect the longitudinal stability of the pusher unit, but which, on account of the flexibility of individual elements in relation to one another, permits an overall flexibility of the pusher unit in all directions. Thus, the pusher assembly, i.e. the combination of catheter tube and of segment-like elements arranged thereon, can be bent relatively easily and thus can be inserted in particular into curved vessels, where the assembly is able to adapt to the anatomy of the vessel. This is achieved by the fact that the pusher unit, which is after all segmented on account of the individual elements threaded onto the catheter tube, is able to execute a bending movement in different directions easily and without compressive loading or force loading. At the same time, as a result of their compact arrangement in series in the longitudinal direction, the segment-like elements, or segments, provide a sufficient pusher force, which is able to counter the force exerted by the pulling-back of the withdrawal sleeve, as in the case of a one-piece stiff pusher catheter tube.

Thus, while the individual segment-like elements of the pusher unit can be made of a relatively stiff material, they nonetheless give the pusher assembly as a whole a high degree of flexibility, since the guide wire catheter can be bent flexibly in the area in which the individual elements are threaded on and where the vascular implant abuts in the loaded state. This signifies an advantageous improvement compared to pusher catheters which are composed of a stiff extruded hose or tube, as in the prior art, and which can be bent only with difficulty and have little flexibility in this area.

It is preferable if the elements are similar, preferably identical, and some elements have a shape that is chosen from among spherical, or substantially spherical, olive-shaped or oval, conical, frustoconical and bell-shaped, wherein the elements moreover have a proximal end and a distal end and a central bore for forming a proximal opening and a distal opening and for forming a channel which is routed through the elements and through which the guide wire catheter tube can be guided.

Here, "substantially" is understood as meaning that the shape of a sphere or of an olive does not have to be strictly adhered to, but that the basic shape of a sphere or olive or of an egg or the like is discernible, and the sphere shape or the olive shape or the like has, however, capped ends for example, a more oval shape with capped ends, and/or round ends, etc.

Through the bore, the individual segment-like elements thus have a distal opening and a proximal opening.

It will be understood in this connection that, in the pusher assembly according to the invention, the shape of the segment-like elements is such that their surface directed outward, i.e. toward the vessel wall, is at least partially curved or rounded, and that they also preferably have a centrally arranged bore through which the catheter tube is guided. The individual elements are thus in fact threaded on like pearls onto a string.

It is preferable if there are at least four individual elements as the pusher unit. In some embodiments of the invention, it is also possible for the individual elements to number fewer than four or else precisely four, or five, six, seven, eight, nine, ten, eleven or twelve. It will be clear to a person skilled in the art that the number of the individual segment-like elements will depend on their respective length and size and also on the insertion system to be used and on the working length thereof, and, finally, also on the vessel that is to be treated. Moreover, after reading the present teaching, it will be clear to a person skilled in the art how many elements have to be present in order to implement the pusher assembly according to the invention.

The material preferably used for the segment-like elements according to the present invention is chosen from at least one of the following: fluorinated ethylene propylene (FEP), polytetrafluoroethylene (PTFE), polyoxymethylene (POM), high-density polyethylene (HDPE) or mixtures thereof. The individual elements can have a hardness of between 60 Shore A and 100 Shore D (the Shore hardness is a known indicator in the prior art for elastomers and polymers), which shows that, with these hard or stiff elements arranged one behind another, no losses are incurred in terms of the longitudinal stability of the pusher unit, and, on the contrary, a higher degree of longitudinal stability can even be achieved.

Here, and throughout the description, a "catheter tube" is understood as meaning any tubular catheter that is normally used in the field of insertion systems for vascular implants to be loaded thereon, and, generally speaking, it is understood as meaning tubes of different diameters and materials, which may vary depending on the application, patient or vessel.

According to a further embodiment of the present invention, it is preferable if at least one of the elements and preferably all the elements have a surface with grooves and/or elongate depressions, wherein the grooves and/or elongate depressions on the surface extend substantially parallel to the catheter tube and therefore parallel to the direction of the vessel.

These features have the advantage that there is only punctiform loading with respect to the withdrawal sleeve that is also guided over the pusher unit, as a result of which less friction is produced when pulling back the withdrawal sleeve and, as a consequence, less force has to be applied by the operator during the pulling-back and release procedure. In this way, an abrupt and/or uneven release is avoided, as a result of which a more precise and easier release of the vascular implant is made possible overall.

According to a further embodiment of the present invention, the individual segment-like elements can further have a coating by which the friction can be further reduced. The coating is preferably chosen from at least one of the following: hydrophilic coating (polyvinyl alcohol), silicon oils or Parylene coating, or mixtures thereof.

The grooves/depressions in the surface of the elements also permit good flushing of the pusher unit, which thus prevents air bubbles from remaining on the surface or from developing there after the flushing procedure. This in turn permits simplified flushing of the insertion device, which represents an essential step prior to introducing the insertion system into a vessel, since the introduction of air into the vessels must be absolutely avoided and prevented.

According to a further embodiment, the elements are not connected or connectable to one another directly and rigidly but instead are merely in abutment with one another or merely lie adjacent to one another on the guide wire catheter tube. When arranging the elements on the guide wire catheter tube, care is taken to ensure that the elements are "threaded on" as compactly as possible and without gaps between them, in order to avoid the pusher unit slipping or to avoid the elements slipping in relation to one another.

Here, and throughout the invention, the term "distal" is understood as meaning that part or portion of the pusher assembly and/or of the insertion system that lies farther away from the operator, and the portion or part that lies nearer to the operator is referred to as being "proximal". Accordingly, the "distal" direction is the direction away from the operator, and the "proximal" direction is the direction toward the operator.

According to a further embodiment, provision can be made that the elements partially engage in one another. According to a further preferred embodiment, the shapes of the segment-like elements are of such a nature that, in the area of the proximal opening provided by the bore in a first segment-like element, a funnel-shaped recess extending inward to the proximal opening is provided, into which recess the distal end or the distal opening of a proximally arranged segment-like element can engage with an exact fit or with a degree of play.

With this embodiment too, it is ensured that the pusher unit composed of the individual elements is sufficiently flexible, since the catheter on which the elements are carried, or threaded, can also still be bent flexibly with these.

According to a further embodiment, provision can be made that the individual elements are connectable to one another by compressive closure. Preferably, a non-releasable annular snap-fit connection is provided here.

According to yet another embodiment of the pusher assembly according to the invention, at least the outermost proximal and/or distal element is fixed rigidly on the catheter tube.

In this embodiment, provision is thus preferably made that at least the farthest proximal element on the catheter tube and/or the farthest distal element on the catheter tube is rigidly connected, preferably glued, to the catheter tube that is guided through them. However, the individual elements are not glued to one another and therefore, according to a preferred embodiment, although they also lie in what is a theoretically displaceable manner on the catheter tube, they are nonetheless positioned non-displaceably on the catheter tube as a result of the compact threading and fixing of the outermost elements or of the outermost element.

The pusher assembly disclosed here and described farther above can also be used in an insertion system for insertion of a vascular implant into a vessel of a patient.

The vessel of the patient can be a blood vessel or else another lumen of the body, for example the bile duct. However, it will be clear to a person skilled in the art that the pusher assembly and the insertion system according to the invention with the pusher assembly according to the invention can be used in a wide variety of vascular implants, in particular stents or stent grafts, a particularly advantageous use being in blood vessels with large diameters.

Accordingly, the present invention also relates to an insertion system for introducing a vascular implant into a vessel of a patient, which insertion system also comprises, in addition to the pusher assembly according to the invention, at least one, preferably several and more preferably all of the following components: a guide wire, a withdrawal sleeve for compressing the vascular implant in the loaded state thereof, and a vascular implant, and also a proximal handling arrangement with which the insertion and release of the vascular implant can be actuated from the proximal direction.

Further advantages and features will become clear from the following description and from the accompanying drawing.

It will be appreciated that the aforementioned features and the features still to be explained below can be used not only in the respectively cited combination but also in other combinations or singly, without departing from the scope of the present invention.

DESCRIPTION OF PREFERRED EMBODIMENTS

Figure 2A:
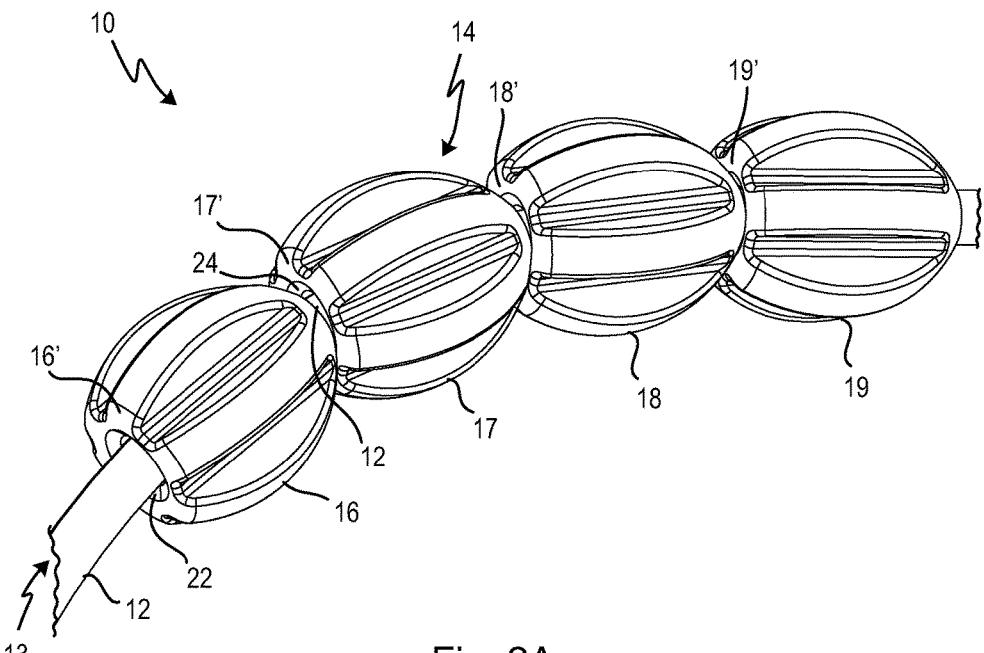
FIGS. 2A-2B shows a schematic representation of an illustrative embodiment of the pusher assembly according to the invention, in a lateral oblique plan view (FIG. 2A) and in a further lateral perspective (FIG. 2B)
Figure 2B:
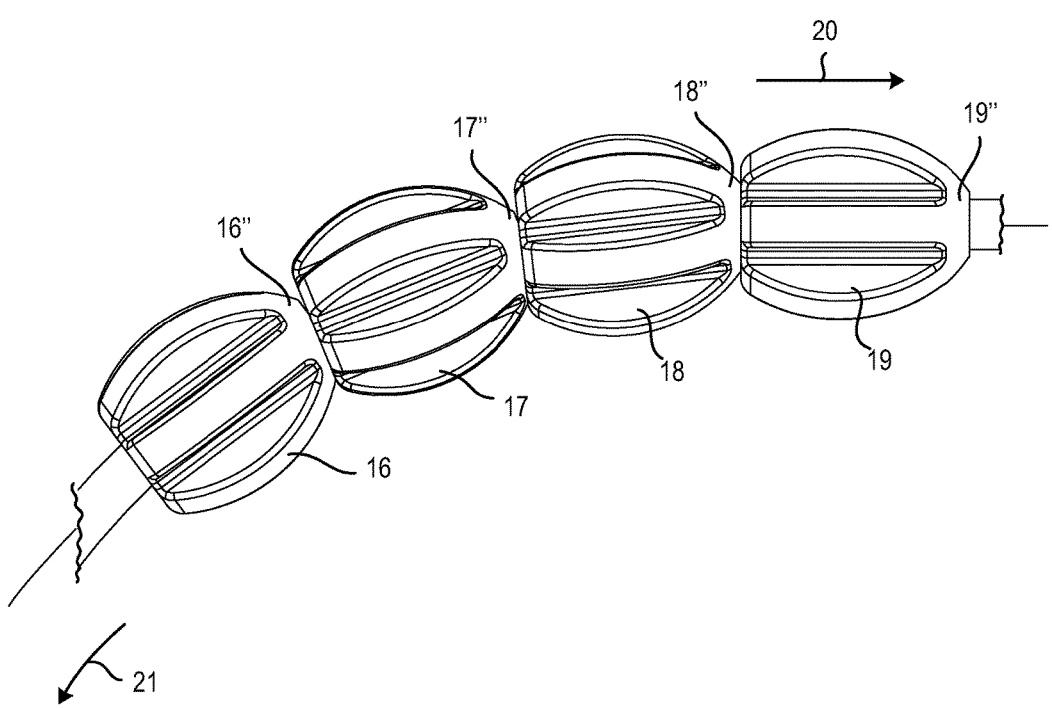

In FIG. 2A, reference number 10 designates overall a pusher assembly having a catheter tube 12 which has a lumen 13 for accommodating a guide wire (not shown), and a pusher unit 14 which, as is shown in FIGS. 2A and 2B, is composed of four individual, segment-like elements 16, 17, 18, 19. It will be appreciated that the pusher unit 14 can also have more elements and is not limited to the number shown in the figures.

A similar view is shown in FIG. 2B, this view being a full side view.

As can be seen from FIG. 2A, the shape of the elements 16, 17, 18, 19 is spherical or oval, or oval in cross section, and the elements 16, 17, 18, 19 thus each have a proximal end 16', 17', 18' and 19' and each have a distal end 16", 17", 18" and 19". The ends 16', 16", 17', 17", 18', 18", 19' and 19" are "blunt" or appear "cut off" or "trimmed".

The elements 16, 17, 18 and 19 each have continuous central bores, for which reason a proximal opening is located at each of the proximal ends 16', 17', 18' and 19', which proximal opening is shown by 22 in FIG. 1A, for example on the basis of the element 16. Moreover, the elements 16, 17, 18 and 19 each have, at their distal end 16", 17", 18" and 19", a distal opening 26, which can be clearly seen in the view of the element 16 in FIG. 1. By way of the bores and openings 22, 26, and by way of the adjoining openings and bores of the elements 17, 18 and 19, the catheter tube 12 is guided through the elements 16, 17, 18 and 19, and the individual elements 16, 17, 18, 19 are thereby threaded on the catheter tube 12.

The arrow 20 in FIG. 2B indicates the distal direction, i.e. the direction leading away from the user or operator, and the arrow 21 indicates the proximal direction, i.e. the direction leading in the direction of the operator.

Figure 1B:
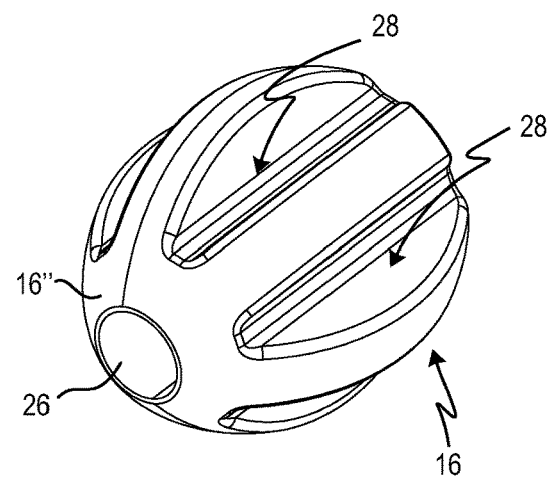
Figure 1C:
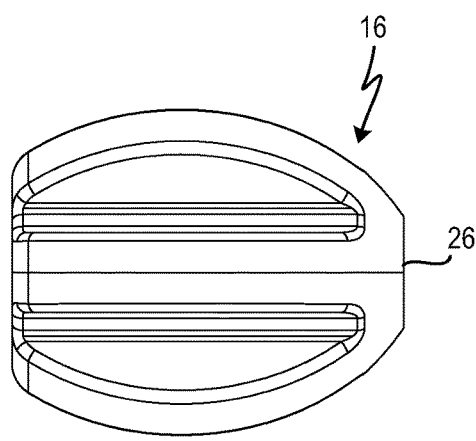

Referring to FIG. 1, the element 16 is shown here on its own, being representative of all the elements 16, 17, 18 and 19, which have identical configurations. However, it will be appreciated, for example, that the outermost distal and/or the outermost proximal element can be designed differently than the other segment-like elements. FIG. 1A shows an oblique perspective view of the proximal opening 22 of the element 16, said opening being provided at the proximal end 16' of the latter. FIG. 1B shows an oblique perspective view of the distal opening 26 at the distal end 16". FIG. 1C, finally, shows a lateral plan view of the element 16 which, in terms of its structure and its size, is identical to the other elements 17, 18 and 19.

It will be seen from FIG. 1A that, around the proximal opening 22 at the proximal end 16', a recess 24 is formed which extends inward in a funnel shape toward the opening. From FIG. 1B, which shows the distal opening 26 at the distal end 16" of the element 16, it will be seen that this end 16" has no such funnel-like recess or cutting or edge that extends toward the opening 26. The distal opening 26, also located in the same form on the elements 17, 18 and 19, or the distal end 16" is adapted precisely in shape to the adjoining proximal end 17' of the next element 17 and thus engages partially or slightly in the funnel-shaped cutting 24 at the proximal end 17' of the next element 17, as a result of which a continuous channel for the catheter tube 12 is in practice formed through both elements 16, 17. At the same time, the elements adjoining via the openings 22 and 26 acquire, in particular also as a result of the funnel-like cutting, a certain movement clearance, which provides the flexibility of the pusher unit 14. The further elements 18 and 19 are arranged in series, or "threaded" onto the catheter tube 12, in the same way.

It will moreover be seen from FIGS. 1 to 3 that the elements 16, 17, 18 and 19 have grooves or elongate depressions 28 in their surface directed toward the outside and toward the vessel wall, which grooves or elongate depressions 28 are introduced like notches into the form of the elements 16, 17, 18 and 19. In the example shown in the figures, the grooves 28 are provided at uniform circumferential intervals on the surface of the elements 16, 17, 18 and 19, wherein six grooves 28 are provided for each of the elements 16, 17, 18 and 19 in the example shown in the figures, and uniformly spaced depressions and elevations are formed by said grooves 28.

As a result of these grooves 28 in the outwardly directed surface of the elements 16, 17, 18 and 19, the overall contact face with which the pusher unit 14 comes into contact with a withdrawal sleeve (see reference sign 40 in FIGS. 3A and 3B) is greatly reduced by comparison with a surface of a pusher unit that has no grooves or depressions 28 and no individual rounded elements.

The grooves or depressions 28 are parallel to the catheter tube guided through the element and are routed from the proximal end 22 to the distal end 22 and are thus also parallel to the vessel and, if appropriate, blood flow.

The arrangement of the elements 16, 17, 18 and 19 in series is shown in FIGS. 2A and 2B. It will be seen that the individual elements 16, 17, 18 and 19 are arranged directly one behind another in such a way that the distal end 16" of a first element 16 is partially introduced into or partially engages in the recess or cutting 24 extending in a funnel shape toward the proximal opening 22 in the proximal end 17' of the second element 17. The elements 16 and 17 thus directly abut each other.

FIG. 3, finally, shows the pusher assembly from FIGS. 1 and 2 with a vascular implant 30 loaded on a distal portion of the catheter tube 12 (indicated by broken lines in FIGS. 3A and 3B for clarity), the distal end 32 of which vascular implant 30 bears directly on the distal end of the element 19. The vascular implant 30 shown by way of example in FIG. 3 is a stent graft with successive stent rings 33 made of self-expanding material, and with an implant material 35 connecting these stent rings 33.

In FIG. 3A, a withdrawal sleeve 40 holds the vascular implant 30 in the compressed state and in so doing also surrounds the individual elements 16, 17, 18, 19, which constitute the pusher unit 14, and also the catheter tube 12 guided centrally through the elements 16, 17, 18, 19 and through the bores and openings 22, 26 thereof. The withdrawal sleeve 40 is routed as far as the proximal handling end (not shown) of the insertion system and connected thereto, and it can be actuated from the proximal handling end of the insertion system.

FIG. 3B shows a first step in the release of the vascular implant 30. Here, by comparison with FIG. 3A, the withdrawal sleeve 40 has already been pulled a distance in the proximal direction 21 in order to release the vascular implant 30. When pulling back the withdrawal sleeve 40, the operator has to apply a certain force, since the withdrawal sleeve, on account of its compressive action, exerts quite considerable forces on the vascular implant 30 and since, in addition, during the pulling back, frictional forces arise between the withdrawal sleeve 40 and the vascular implant and the pusher assembly.

It will now be seen from FIG. 3B that, after a first step of pulling back the withdrawal sleeve 40 in the proximal direction 22, the vascular implant is radially expanded at its distal end 34, where it is no longer held compressed by the withdrawal sleeve, and it can position itself on the vessel wall (not shown) and anchor itself there. As the withdrawal sleeve 40 is being pulled back, the pusher unit 14, formed by the elements 16, 17, 18 and 19 and with good longitudinal stability, counteracts the forces that occur during the pulling back of the withdrawal sleeve 40, and it thereby holds the vascular implant 30 at the correct position in the vessel.

After the vascular implant 30 has been fully released, the pusher unit 14 or the pusher assembly 10, or rather the insertion system as such, can be removed from the vessel.

What is claimed is:

1. An insertion system comprising a vascular implant and a pusher assembly for the vascular implant, wherein the pusher assembly has a catheter tube which has a lumen for accommodating a guide wire and which has a proximal catheter tube portion and, adjoining the latter, a distal catheter tube portion, wherein the distal catheter tube portion is provided at least partially for movably accommodating the vascular implant thereon, and wherein the catheter tube moreover has a pusher unit for releasing the vascular implant, said pusher unit being proximally adjacent to the vascular implant loaded onto the catheter tube, wherein the pusher unit is formed by individual, segment-like elements, which are arranged one behind another and adjacent to one another on the catheter tube and proximally adjacent to the vascular implant, such that a distal most one of the pusher unit elements pushes on a proximal end of the vascular implant;

wherein the elements are threaded onto the catheter tube;

wherein the individual elements have a shape that is chosen from spherical, or substantially spherical, oval, conical, frustoconical, and bell-shaped;

wherein the elements are in direct contact with one another but are not fixed directly to one another, such that the elements form articulable joints between one another; and wherein the elements moreover have a proximal end and a distal end and a central bore for forming a proximal opening and a distal opening and for forming a channel which is routed through the elements and through which the elements are threaded onto the catheter tube, thereby guiding the catheter tube through the elements.

2. The insertion system of claim 1, wherein the elements are at least similar, preferably identical.

3. The insertion system of claim 1, wherein at least four elements are provided.

4. The insertion system of claim 1, wherein at least one of the elements has grooves on its surface directed toward the vessel wall, wherein the grooves on the surface extend substantially parallel to the catheter tube and from a proximal end to a distal end of the elements.

5. The insertion system of claim 1, wherein the elements partially engage in one another.

6. The insertion system of claim 1, wherein a funnel-shaped recess extending inward to the proximal opening is provided on the proximal end of an element.

7. The insertion system of claim 1, wherein the individual elements are connectable to one another by compressive closure.

8. The insertion system of claim 1, wherein at least the outermost proximal and/or distal element is fixed rigidly on the catheter tube.

9. The insertion system of claim 1, wherein it moreover has one of the following: a guide wire, and a withdrawal sleeve for compressing the vascular implant in the loaded state thereof.

* * * * *